(12) United States Patent
Thornton

(10) Patent No.: US 6,718,199 B2
(45) Date of Patent: Apr. 6, 2004

(54) MEASUREMENT OF ELECTROPHYSIOLOGIC RESPONSE

(75) Inventor: Aaron Thornton, West Des Moines, IA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 122 days.

(21) Appl. No.: 10/014,274

(22) Filed: Oct. 26, 2001

(65) Prior Publication Data
US 2002/0052561 A1 May 2, 2002

Related U.S. Application Data

(60) Provisional application No. 60/243,682, filed on Oct. 27, 2000.

(51) Int. Cl.[7] .............................................. A61B 5/04
(52) U.S. Cl. ..................... 600/544; 600/300; 600/546; 600/547
(58) Field of Search ................................ 600/300–301, 600/544–547

(56) References Cited

U.S. PATENT DOCUMENTS

| | | | |
|---|---|---|---|
| 4,979,214 A | * 12/1990 | Hamilton | 704/233 |
| 5,154,180 A | 10/1992 | Blanchet et al. | 128/731 |
| 5,458,117 A | * 10/1995 | Chamoun et al. | 600/547 |
| 5,632,272 A | * 5/1997 | Diab et al. | 600/323 |
| 6,071,246 A | 6/2000 | Sturzebecher et al. | 600/559 |
| 6,117,074 A | 9/2000 | Schurmann et al. | 600/300 |
| 6,306,100 B1 | * 10/2001 | Prass | 600/554 |

FOREIGN PATENT DOCUMENTS

| | | | |
|---|---|---|---|
| DE | 196 08 734 | 5/1997 | G06F/17/15 |
| EP | 0 898 234 | 2/1999 | G06F/17/00 |

OTHER PUBLICATIONS

International Search Report date mailed Jun. 8, 2002.

* cited by examiner

Primary Examiner—Robert L. Nasser
Assistant Examiner—Patricia C Mallari
(74) Attorney, Agent, or Firm—Fish & Richardson P.C.

(57) ABSTRACT

A method for estimating an electrophysiologic response contained in a measured signal includes obtaining a plurality of samples and defining a plurality of bins, each of which corresponds to a range of values of a sorting parameter associated with each of the samples. Each sample of the measured signal is then classified into one of the bins on the basis of a value of a sorting parameter associated with that sample. Then, for each bin, a statistic indicative of samples classified into that bin is maintained. On the basis of these bin statistics, the desired electrophysiologic response can then be estimated.

31 Claims, 3 Drawing Sheets

MEASUREMENT OF ELECTROPHYSIOLOGIC RESPONSE

RELATED APPLICATIONS

This application claims the benefit of the priority date of U.S. Provisional Application No. 60/243,682, filed on Oct. 27, 2000, the contents of which are herein incorporated by reference.

FIELD OF INVENTION

The invention relates to the measurement of electrophysiologic responses, and more particularly to enhancing the signal-to-noise ratio in such measurements.

BACKGROUND

In making a diagnosis, it is often useful to have the patient's cooperation. This is particularly true in the diagnosis of disease involving sensory pathways to the brain. For example, a straightforward way to assess a patient's hearing is to simply ask the patient whether he can hear particular tones having various frequencies and amplitudes.

In many cases, one takes for granted that a patient will be able to answer such questions. However, in some cases, a patient cannot communicate his perception. This occurs most frequently when the patient is an infant, or when the patient is unconscious. In a veterinary setting, it is rare to encounter a patient that can accurately communicate perception at all.

One approach to evaluating an infant's hearing is to make a sound and to then measure an evoked response associated with that sound. This evoked response is typically an electrophysiologic signal generated in response to the sound and traveling between the inner ear and the brain along various neural pathways, one of which includes the auditory brainstem. This signal is thus referred to as the "auditory brainstem-response," hereafter referred to as the "ABR."

The ABR is typically only a small component of any measured electrophysiologic signal. In most cases, a noise component arising from other, predominantly myogenic, activity within the patient dwarfs the ABR. The amplitude of the ABR typically ranges from approximately 1 microvolt, for easily audible sounds, to as low as 20 nanovolts, for sounds at the threshold of normal hearing. The noise amplitude present in a measured electrophysiologic signal, however, is typically much larger. Typical noise levels range from between 2 microvolts to as much as 2 millivolts. The resulting signal-to-noise ratio is thus between −6 dB and −100 dB One approach to increasing the signal-to-noise ratio is to exploit differences between the additive properties of the ABR and that of the background noise. This typically includes applying a repetitive auditory stimulus (a series of clicks, for example) and sampling the electrophysiologic signal following each such stimulus. The resulting samples are then averaged. The ABR component of the samples add linearly, whereas the background electrophysiologic noise, being essentially random, does not. As a result, the effect of noise tends to diminish with the number of samples. The number of samples required to reach a specified signal-to-noise level depends on the noise level present in the samples. In principle, therefore, one can achieve a specified signal-to-noise ratio either with a small number of relatively quiet samples or with a large number of relatively noisy samples.

In practice, signal averaging techniques such as that described above are unlikely to work when the signal-to-noise ratio is worse than −48 dB. Since a minimally acceptable 5% confidence level requires a signal-to-noise ratio of at least −4 dB, this signal-averaging approach is prone to inaccuracy.

Signal averaging methods as described above perform best when the background noise is relatively constant. For example, the steady drone of an air-conditioner can readily be separated from a signal of interest. Such background noise is referred to as "stationary" noise.

The noise component of an electrophysiologic signal is often non-stationary. For example, after a few minutes of taking measurements, an infant may begin to stir, thereby momentarily increasing the background electrophysiologic noise level. The infant might then return to a deep sleep, thereby reducing the background electrophysiologic noise level.

The non-stationary nature of the noise component poses a dilemma for a clinician attempting to measure the ABR. For example, if the infant begins to stir, the clinician might suspend taking measurements to avoid contaminating data already collected with noisy data. This might prove to be a good decision if the infant were to fall back into a deep sleep, since one could then acquire additional quiet samples. However, even noisy samples can improve signal-to-noise ratio, provided that there are enough of them available. Hence, this might also prove to be a poor decision if the infant were to continue stirring. In such a case, it would have been better to have acquired the additional, albeit noisy samples. Because the behavior of an infant is, to a great extent, unpredictable, the clinician occasionally makes an incorrect guess, thereby either wasting time or needlessly corrupting acquired data.

SUMMARY

The invention is based on the recognition that, by dividing the sequence of samples that make up the signal into subsequences of samples, one can reduce the signal-to-noise ratio of an electrophysiologic signal and avoid many difficulties posed by the presence of non-stationary noise. The samples within a particular subsequence are characterized by a common range of values of a sorting parameter. Each subsequence of samples yields a statistic that is independent of corresponding statistics yielded by other subsequences of samples. These statistics, each of which corresponds to a subsequence, can then be combined in different ways to derive an estimate of an electrophysiologic response contained in the signal. The presence of non-stationary noise can, to a great extent, be compensated for by appropriately combining the statistics associated with each subsequence.

In one practice of the invention, a plurality of samples of a measured electrophysiologic signal is obtained. The electrophysiologic signal typically includes an electrophysiologic response to a stimulus. The method of the invention seeks to estimate the value of this response.

The method includes defining a plurality of bins, each of which corresponds to a range of values of a sorting parameter associated with each of the samples. Preferably, the range of values for each bin is such that each value of the sorting parameter is associated with at most one bin.

Each sample of the measured signal is then classified into one of the bins on the basis of a value of a sorting parameter associated with that sample. Then, for each bin, a statistic indicative of samples classified into that bin is maintained. On the basis of these bin statistics, the desired electrophysiologic response can then be estimated. In one particular practice of the invention, maintaining the bin statistic includes maintaining a moving average of samples in the bin.

In one practice of the invention, the sorting parameter includes a measure of noise present in the samples. The noise might be electrophysiologic noise, ambient acoustic noise, or any other noise process. The sorting parameter can also be derived from a combination of noise processes.

The estimation of electrophysiologic response can include combining the bin statistics to derive a quantity indicative of the electrophysiologic response. This might include averaging the bin statistics, or evaluating a weighted averaging of the bin statistics, with the weights being manually or automatically selected. In one practice, the weight assigned to a statistic for samples in a particular bin might be indicative of a quality of the samples in the bin. For example, the weight can be inversely proportional to a noise level associated with the particular bin. Alternatively, the weights can be selected to optimize a measure of an extent to which the quantity approximates the electrophysiologic response. The assignment of weights in a weighted average can also include excluding bin statistics associated with particular bins from being considered in evaluating the quantity indicative of the electrophysiologic response.

In another practice of the invention, a sequence of samples is decomposed into a plurality of subsequences, each of which includes samples selected on the basis of a value of a sorting parameter associated with each of the samples. The samples from each subsequence are then used to evaluate a plurality of subsequence statistics, each of which is associated with a corresponding subsequence. A subset of these subsequence statistics is then selected. The subset can include some or all of the subsequence statistics. On the basis of subsequence statistics from this set, the electrophysiologic response is then estimated.

In one practice of the invention, the subsequences are selected by selecting a noise threshold. Subsequence statistics that are associated with subsequences having noise levels above this threshold are then excluded from the subset.

The extent to which each of the selected subsequence statistics contributes to an estimate of the electrophysiologic response can be controlled. For example, one or more subsequence statistics can be weighted by an amount indicative of noise present in the corresponding subsequence. In this optional practice of the invention, subsequences statistics from subsequences that contain exceptionally noisy samples can be made to contribute less to the estimate than subsequence statistics from subsequences having samples that are not as noisy.

The method of the invention is applicable to various types of physiological stimuli. These stimuli include auditory, visual, olfactory, and gustatory stimuli, or combinations thereof.

These and other features and advantages of the invention will better understood from the following detailed description and the accompanying figures, in which:

DETAILED DESCRIPTION

Figure 1:
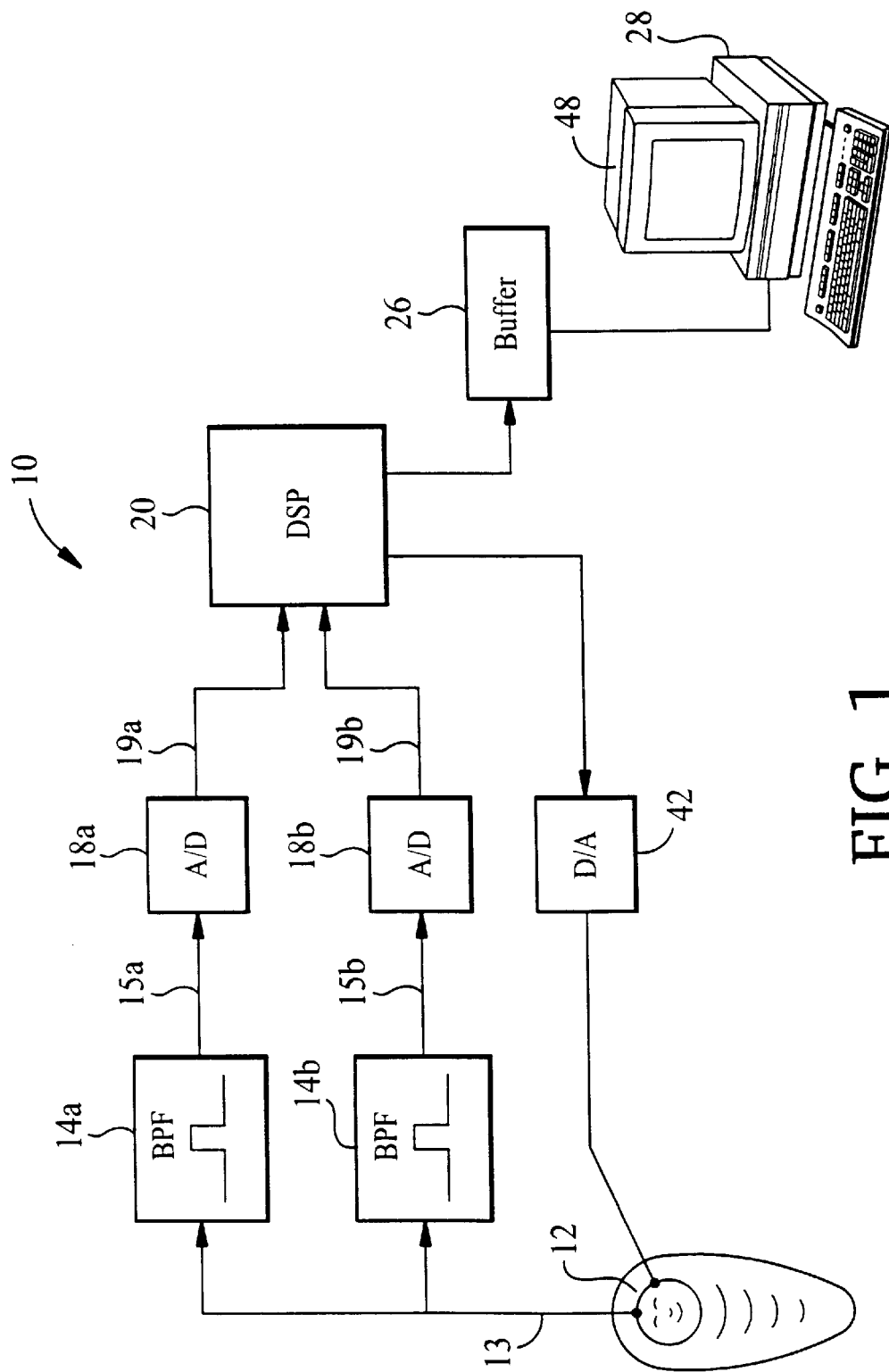
FIG. 1 is a block diagram of a system for acquiring electrophysiologic data.

Referring to FIG. 1, a system 10 for acquiring electrophysiologic data for measurement of auditory brainstem response ("ABR") includes a sensor 12 attached to an infant's scalp. The sensors 12, which are typically scalp electrodes, are configured to detect an analog signal 13 representing ongoing electrical activity. This analog signal 13 is provided to first and second band-pass filters 14a–b that generate first and second filtered signals 15a–b, respectively. In one embodiment, the first band-pass filter 14a has a passband between 180 Hz and 2000 Hz and the second band-pass filter 14b has a passband between 30 Hz and 2000 Hz. The resulting first and second filtered signals 15a–b are then passed to first and second analog-to-digital (A/D) converters 18a–b for conversion into a corresponding first and second digital signals 19a–b. These digital signals 19a–b are then provided to a digital signal processor 20.

Figure 2:
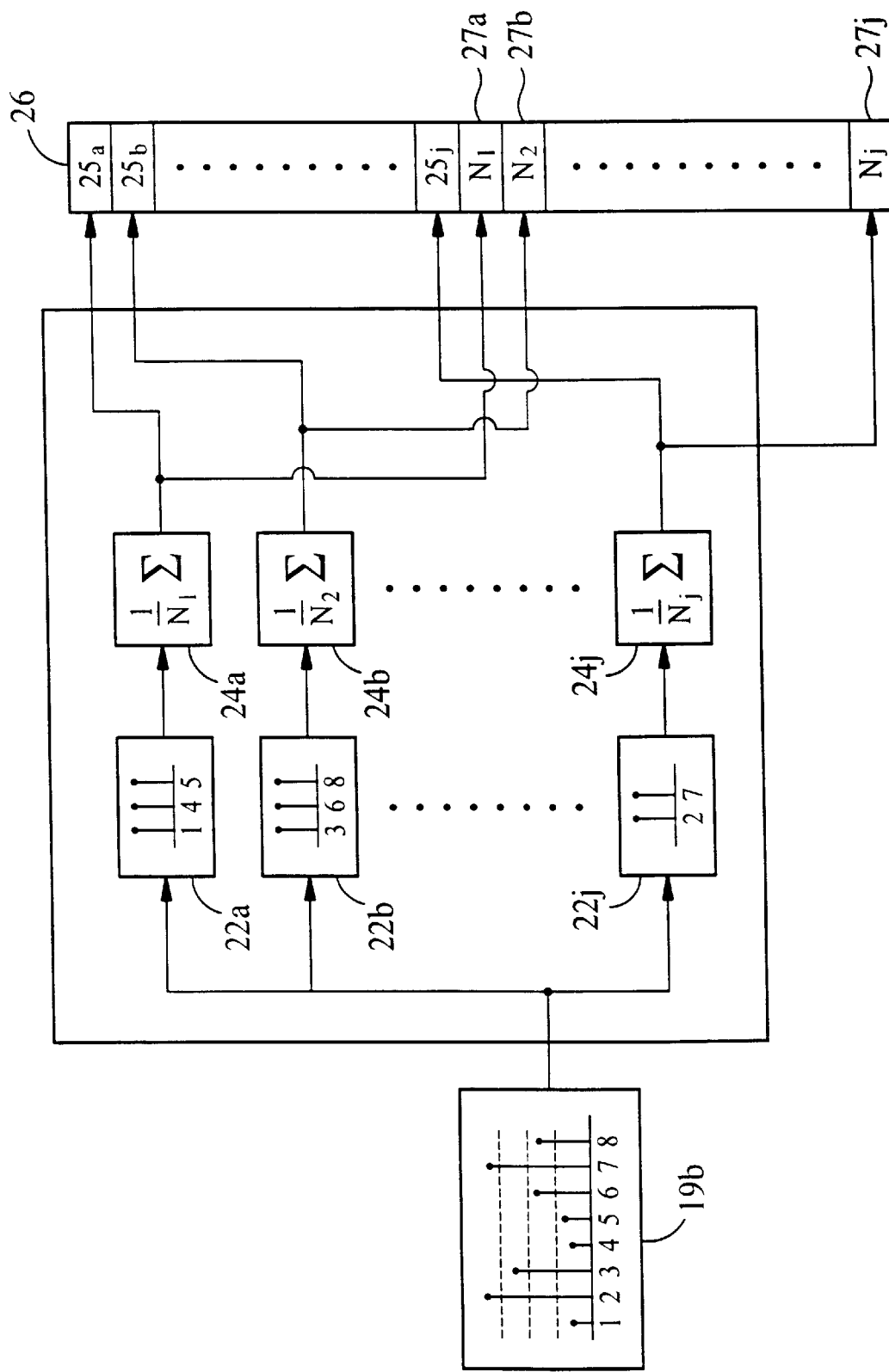
FIGS. 2 and 3 illustrate the data acquisition process.

Referring now to FIG. 2, on the basis of noise measurements derived from the first digital signal 19a, the digital signal processor 20 sorts the samples that make up the second digital signal 19b into a plurality of bins 22a–j each of which is associated with a band of noise amplitudes. The amplitude bands of the bins 22a–j are selected to be non-overlapping. For the application described herein, there are ten bins. However, the number of bins 22a–j, and the amplitude ranges associated with each bin 22a–j, depend on the specific application of the data-acquisition system 10. Each bin 22a–j has an associated averaging accumulator 24a–j that maintains a moving average 25a–j of the samples in its corresponding bin 22a–j. Each bin 22a–j also has an associated counter 27a–j that contains the number of samples $N_i$ in its associated bin 22a–j. Referring back to FIG. 1, the moving averages 25a–j and the counters 27a–j are maintained in a data buffer 26 that is available to a processing system 28.

Note that the first and second digital signals 19a–b need not use the same time-base. For example, the first A/D converter 18a might sample the first filtered signal 15a at a sampling rate that differs from that used by the second A/D converter 18b to sample the second filtered signal 15b. In another example, the noise analysis may be made over a portion of the first filtered signal 15a that corresponds to a time interval that precedes and/or follows the portion of the second filtered signal 15b that corresponds to a time interval including the data being sorted into one of the bins. Additionally, noise analysis of a portion of the first filtered signal 15a can impact the sorting of samples from several portions of the second filtered signal 15b. The method of the invention can thus be used with any manner of noise analysis.

During data acquisition, each averaging accumulator 24a averages only those samples within its associated bin 22a. Since all samples are within one of the bins 22a–j, each sample can affect no more than one moving average 25a–j. Since the samples in any one bin 22a are averaged independently of samples in other bins 22b–j, samples from one bin 22a are prevented from contaminating the moving averages 25b–j obtained by averaging samples from other bins 22b–j.

Figure 3:
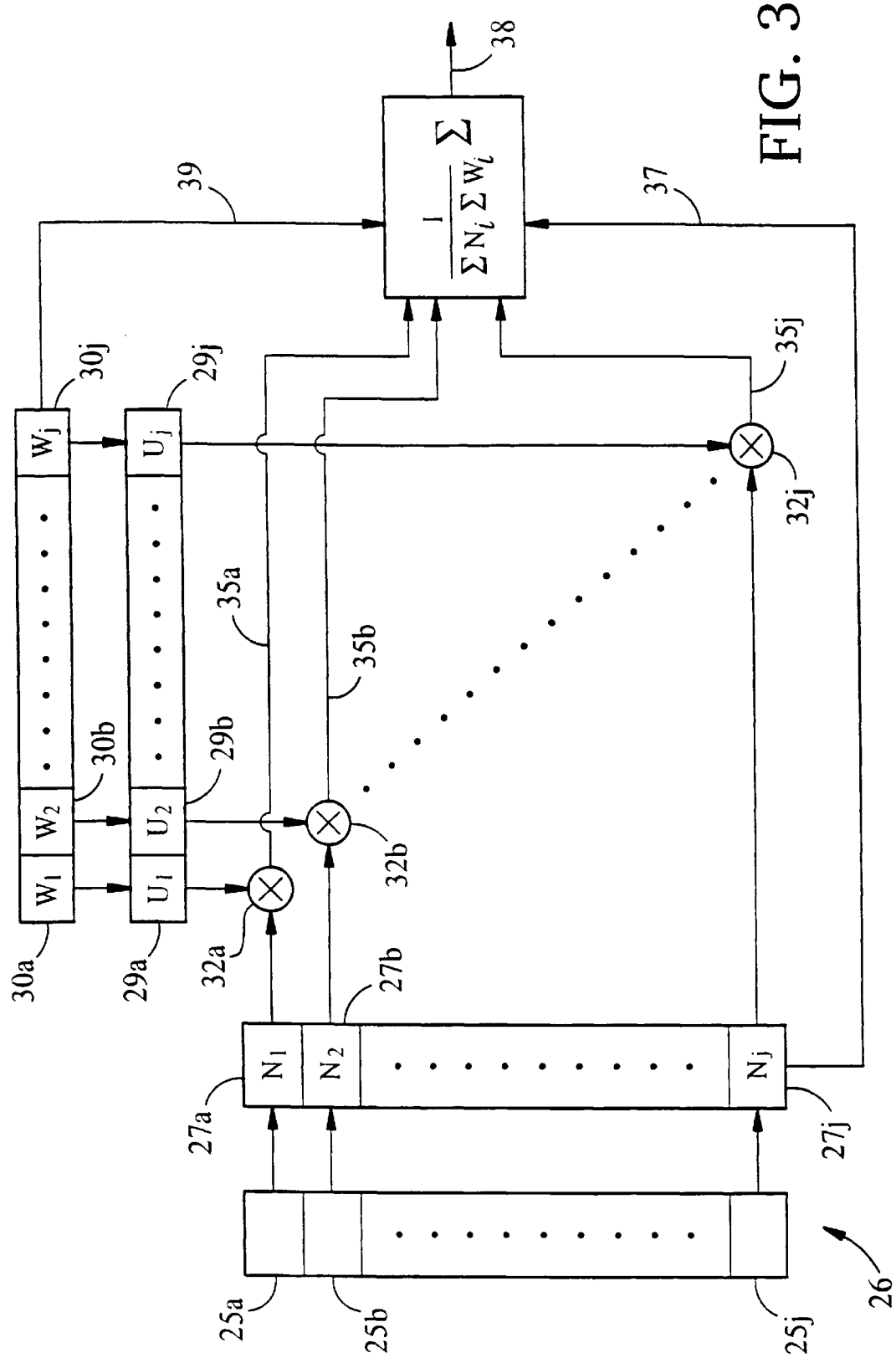

Referring now to FIG. 3, the clinician can, at any time select which of the moving averages 25a–j available for each band are to be combined into a single average representative of an ABR measurement 38. As shown in FIG. 3, the clinician controls switches $u_i$ 29a–j that selectively exclude selected bands (hereafter referred to as "excluded bands") from consideration in evaluating the ABR measurement 38. These switches 29a–j are typically set to exclude from consideration all bands having a noise power above a selected threshold.

The clinician also controls weighting coefficients 30a–j associated with each of the remaining bands (hereafter referred to as the "included" bands). These weighting coefficients 30a–j can be controlled manually, or automatically. In either case, weighting coefficients 30a–j can be controlled individually, or as a group. Additionally, particular combinations of weighting coefficients 30a–j can be preprogrammed and selectively applied.

The moving averages 25a–j of each included band, which are available in the accumulators 24a–j, are then multiplied by the corresponding number of samples $N_l$ in each band. The results are then scaled by their corresponding weighting coefficients 30a–j at corresponding mixers 32a–j. The outputs 35a–j of the mixers 32a–j, which are proportional to the weighted averages 34a–j corresponding to each band, the accumulated number of samples summed across all included bands, and the sum of the weighting coefficients of the included bands, are then provided to an output averaging-element 36, the output of which is the desired ABR measurement 38. This ABR measurement 38 is obtained by summing the outputs of the mixers 32a–j and normalizing the result by both the sum of the weighting coefficients of the included bands and the accumulated number of samples summed across the included bands.

In the illustrated embodiment, the processing system 28 carries out the function of mixing the moving averages 25a–j with the weighting coefficients 30a–c, averaging the resulting products, and normalizing the result to obtain the desired ABR measurement 38. However, without loss of generality, these functions can also be carried out by special-purpose hardware.

In one practice of the invention, the data associated with each included band is weighted by the reciprocal of the noise amplitude associated with that band. As a result, data from noisier included bands will contribute less to the ABR measurement 38 than data from less noisy included bands. This reduces the possibility that contributions from noisier included bands will excessively degrade the accuracy of the ABR measurement 38.

In addition to processing the amplified signal received from the sensors, the digital signal processor 20 also generates repetitive auditory stimuli. These auditory stimuli are communicated to the infant through an earphone 40 in communication with the digital signal processor 20 by way of a digital-to-analog (D/A) converter 42, as shown in FIG. 1. The auditory stimuli can be adaptively controlled by the digital signal processor 20 in response to the measurements obtained by the data-acquisition system 10. For example, if no ABR response appears to be evoked, the digital signal processor 20 may gradually increase the amplitude of the auditory stimuli to identify the infant's hearing threshold.

The processing system 28 also executes user-interface software for displaying, on a display monitor 48, the results of data manipulation performed by the digital signal processor 20. In the illustrated embodiment, the processing system 28 uses a Windows NT® operating system to execute user-interface software necessary for convenient display of data.

The data-acquisition system 10 permits retrospective control over which bands to incorporate into the ABR measurement 38 and the extent to which each band contributes to the ABR measurement 38. By judiciously selecting the weighting coefficients 30a–j, the signal-to-noise ratio of the ABR measurement can be optimized even in the presence of non-stationary electrophysiologic noise. As the ABR measurement 38 unfolds during the data acquisition process, the weighting coefficients 30a–j can be adjusted in an effort to maximize the signal-to-noise ratio of the ABR measurement 38. These adjustments can be made either in real-time, while the test is being conducted, or after the test has been terminated. The clinician conducting the test can thus experiment with different weighting coefficients 30a–j without discarding valuable data and/or unnecessarily replicating data.

Clinical ABR testing often results in multiple tests of the same stimulus condition, with measurements from each test being contaminated by different patterns of background nose. For example, in the middle of one test, a doctor's pager may suddenly go off, while in the middle of another test, the infant may cough or sneeze.

Previously, it was counterproductive to combine data from a relatively noiseless test with data from a test having greater average noise. The data-acquisition system 10 described herein, however, permits data to be combined band by band across several such tests in a manner that optimizes the signal-to-noise ratio of the resulting ABR measurement 38.

In conventional data-acquisition systems, weighted averaging requires a priori selection of weighting coefficients. Thus, the weighting coefficients cannot be adaptively optimized in response to the signal-to-noise ratio of the resulting ABR measurement. In contrast, the data-acquisition system 10 described herein enables weighting coefficients 30a–j to be assigned dynamically or after the fact, thereby providing considerably more flexibility in the selection of methods for optimizing signal-to-noise ratio of the ABR measurement 38.

The data-acquisition system 10 and method described herein are generally applicable to all clinical ABR testing, whether manual or automated. Such ABR testing can include neuro-diagnostic procedures, audiometric threshold estimation, and newborn screening.

The invention has been described in the context of measuring auditory response. However, evoked responses can arise from other stimuli, such as visual, tactile, olfactory, or gustatory stimuli. The principles described herein are applicable to measurement of evoked response resulting from whatever stimuli.

As described herein, samples are sorted into bins 22a–j on the basis of electrophysiologic noise amplitudes. However, sorting parameters other than electrophysiologic noise amplitude can be used. Additionally, the sorting parameter can also be a multi-dimensional quantity. For example, the digital signal processor 20 may have a second input for measuring ambient acoustic noise level. In such a case, the digital signal processor 20 can assign samples to bins 22a–j on the basis of both an electrophysiologic quantity, namely the sample amplitude, and on an acoustic quantity, namely the measured ambient acoustic noise level in the testing room. In this case, the sorting parameter is a two dimensional quantity and the bins 22a–j can be viewed as a two-dimensional array. While this might complicate the implementation of the data-acquisition system 10, the principle of the invention is itself unchanged.

Alternatively, the sorting parameter can be made a function of more than one variable. For example, a measurement of ambient acoustic noise in the room might be converted into an equivalent electrophysiologic noise level. This equivalent electrophysiologic noise level could then be added to corresponding samples from the digital signal before those signals are sorted into bins 22a–j.

It is to be understood that the foregoing description is intended to illustrate and not limit the scope of the invention. The invention is defined by the scope of the following claims. Other aspects, advantages, and modifications are within the scope of the following claims.

Having described the invention, and a preferred embodiment thereof, what I claim as new, and secured by Letters Patent is:

1. A method of estimating an electrophysiologic response contained in a measured electrophysiologic signal, said method comprising:

obtaining a plurality of samples of said measured electrophysiologic signal;

defining a plurality of bins, each of said bins corresponding to a range of values of said sorting parameter;

for each sample, classifying said sample into one of said bins on the basis of a value of said sorting parameter, said value being associated with said sample;

for each bin, maintaining a bin statistic indicative of samples classified into said bin; and estimating said electrophysiologic response by combining said bin statistics, wherein combining said bin statistics comprises selecting a subset of said bin statistics to derive a quantity indicative of said electrophysiologic response.

2. A method of estimating an electrophysiologic response contained in a measured electrophysiologic signal, said method comprising:

obtaining a plurality of samples of said measured electrophysiologic signal;

defining a plurality of bins, each of said bins corresponding to a range of values of a sorting parameter, said sorting parameter being selected to include a measure of noise in said plurality of samples;

for each sample, classifying said sample into one of said bins on the basis of a value of said sorting parameter, said value being associated with said sample;

for each bin, maintaining a bin statistic indicative of samples classified into said bin; and estimating said electrophysiologic response on the basis of said bin statistics.

3. The method of claim 1, wherein defining a plurality of bins comprises selecting a range of values for each bin such that each value of said sorting parameter is associated with at most one bin.

4. The method of claim 1, wherein selecting said sorting parameter comprises selecting said sorting parameter to include a measure of electrophysiologic noise in said plurality of samples.

5. The method of claim 1, wherein selecting said sorting parameter comprises selecting said sorting parameter to include a measure of ambient acoustic noise associated with said plurality of samples.

6. The method of claim 1, wherein maintaining said bin statistic comprises maintaining a moving average of samples in said bin.

7. The method of claim 1, wherein estimating said electrophysiologic response comprises combining said bin statistics to derive a quantity indicative of said electrophysiologic response.

8. The method of claim 7, wherein combining said bin statistics comprises evaluating an average of said bin statistics.

9. The method of claim 8, wherein evaluating an average of said bin statistics comprises evaluating a weighted average of said bin statistics.

10. The method of claim 7, wherein combining said bin statistics comprises selecting a subset of said bin statistics for deriving said quantity indicative of said electrophysiologic response.

11. The method of claim 7, wherein combining said bin statistics comprises selecting weights to apply to each of said bin statistics.

12. The method of claim 11, wherein selecting said weights comprises selecting said weights to optimize a measure of an extent to which said quantity approximates said electrophysiologic response.

13. The method of claim 11, wherein selecting said weights comprises selecting said weights on the basis of a measure of a quality of samples in bins corresponding to each of said weights.

14. The method of claim 13, wherein selecting said weights on the basis of a measure of quality comprises assigning a weight to a particular bin on the basis of noise associated with samples in said particular bin.

15. A method of estimating an electrophysiologic response contained in a measured electrophysiologic signal, said method comprising:

obtaining a plurality of samples of said measured electrophysiologic signal;

defining a plurality of bins, each of said bins corresponding to a range of values of a sorting parameter;

for each sample, classifying said sample into one of said bins on the basis of a value of said sorting parameter, said value being associated with said sample;

for each bin, maintaining a bin statistic indicative of samples classified into said bin; and estimating said electrophysiologic response by combining said bin statistics, wherein combining said bin statistics comprises selecting weights to apply to each of said bin statistics, said weights being selected to optimize a measure of an extent to which said quantity approximates said electrophysiologic response.

16. A system for estimating an electrophysiologic response contained in a measured electrophysiologic signal, said system comprising:

a digital signal processor configured to receive samples of said measured electrophysiologic signal to define a plurality of bins, each of said bins corresponding to a range of a sorting parameter; to classify each of said samples into one of said bins on the basis of a value of said sorting parameter, said value being associated with said sample, and to maintain a plurality of bin statistics, each of said bin statistics being indicative of samples classified into a corresponding bin, said digital signal processor including a noise analyzer for evaluating noise in said plurality of samples;

a memory element in communication with said digital signal processor, said memory element being configured to store said bin statistics; and a processing element in communication with said memory element, said processing element being configured to estimate said electrophysiologic response on the basis of said bin statistics.

17. The system of claim 16, wherein said digital signal processor is configured to select a range of values for each bin such that each value of said sorting parameter is associated with at most one bin.

18. The system of claim 16, wherein said noise analyzer is configured to evaluate a measure of electrophysiologic noise in said plurality of samples.

19. The system of claim 16, wherein said noise analyzer is configured to evaluate a measure of ambient acoustic noise associated with said plurality of samples.

20. The system of claim 15, wherein said digital signal processor is configured to maintain a moving average of samples in said bin.

21. The system of claim 15, wherein said processing element is configured to estimate said electrophysiologic response by combining said bin statistics to derive a quantity indicative of said electrophysiologic response.

22. The system of claim 21, wherein said processing element is configured to evaluate an average of said bin statistics.

23. The system of claim 22, wherein said processing element is configured to evaluate a weighted average of said bin statistics.

24. The system of claim 21, wherein said processing element is configured to select a subset of said bin statistics for deriving said quantity indicative of said electrophysiologic response.

25. The system of claim 21, wherein said processing element is configured to select weights to apply to each of said bin statistics.

26. The system of claim 25, wherein said processing element is configured to select said weights on the basis of a measure of a quality of samples in bins corresponding to each of said weights.

27. The system of claim 26, wherein said processing element is configured to assign a weight to a particular bin on the basis of noise associated with samples in said particular bin.

28. The system of claim 15, wherein said digital signal processor comprises a general purpose digital computer.

29. A method of estimating an electrophysiologic response contained in a measured electrophysiologic signal, said method comprising:

obtaining a plurality of samples of said measured electrophysiologic signal;

defining a plurality of bins, each of said bins corresponding to a range of values of a sorting parameter;

for each sample, classifying said sample into one of said bins on the basis of a value of said sorting parameter, said value being associated with said sample;

for each bin, maintaining a bin statistic indicative of samples classified into said bin; and estimating said electrophysiologic response by combining said bin statistics, wherein combining said bin statistics includes selecting weights to apply to each of said bin statistics, said weights being selected on the basis of a measure of a quality of samples in bins corresponding to each of said weights.

30. A system for estimating an electrophysiologic response contained in a measured electrophysiologic signal, said system comprising:

a digital signal processor configured to receive samples of said measured electrophysiologic signal to define a plurality of bins, each of said bins corresponding to a range of a sorting parameter; to classify each of said samples into one of said bins on the basis of a value of said sorting parameter, said value being associated with said sample, and to maintain a plurality of bin statistics, each of said bin statistics being indicative of samples classified into a corresponding bin;

a memory element in communication with said digital signal processor, said memory element being configured to store said bin statistics; and a processing element in communication with said memory element, said processing element being configured to estimate said electrophysiologic response by combining bin statistics to derive a quantity indicative of said electrophysiological response, said quantity being derived by selecting a subset of said bin statistics for deriving a quantity indicative of said electrophysiologic response.

31. A system for estimating an electrophysiologic response contained in a measured electrophysiologic signal, said system comprising:

a digital signal processor configured to receive samples of said measured electrophysiologic signal to define a plurality of bins, each of said bins corresponding to a range of a sorting parameter; to classify each of said samples into one of said bins on the basis of a value of said sorting parameter, said value being associated with said sample, and to maintain a plurality of bin statistics, each of said bin statistics being indicative of samples classified into a corresponding bin;

a memory element in communication with said digital signal processor, said memory element being configured to store said bin statistics; and a processing element in communication with said memory element, said processing element being configured to estimate said electrophysiologic response by combining bin statistics to derive a quantity indicative of said electrophysiological response, said quantity being derived by selecting weights to apply to each of said bin statistics, said weights being selected on the basis of a measure of a quality of samples in bins corresponding to each of said weights.

* * * * *